United States Patent [19]

Arnold et al.

[11] Patent Number: 4,569,222
[45] Date of Patent: Feb. 11, 1986

[54] ROLLING CASTER FLOOR TESTER

[75] Inventors: Marlene R. Arnold, Bainbridge; George E. Gard, Columbia, both of Pa.

[73] Assignee: Armstrong World Industries, Inc., Lancaster, Pa.

[21] Appl. No.: 685,401

[22] Filed: Dec. 24, 1984

[51] Int. Cl.⁴ .......................................... G01N 19/02
[52] U.S. Cl. .......................................... 73/9; 73/822
[58] Field of Search ................ 73/7, 8, 9, 78, 81, 73/822

[56] References Cited

U.S. PATENT DOCUMENTS 3,364,726 1/1968 Bonham .................................. 73/7
3,854,328 12/1974 Schmidt ............................. 73/822

FOREIGN PATENT DOCUMENTS 213507 9/1984 German Democratic Rep. ...... 73/7

Primary Examiner—S. Clement Swisher

[57] ABSTRACT

An apparatus for testing the friction and susceptibility to damage by casters of various floor materials. A sample of floor material is moved under a caster wheel by a moving table. The caster orientation, pressure and size are variable. Forces on the caster are monitored by instruments which also read the reaction of the floor sample to the test. Records are produced both in tabular and in graphic form.

9 Claims, 1 Drawing Figure

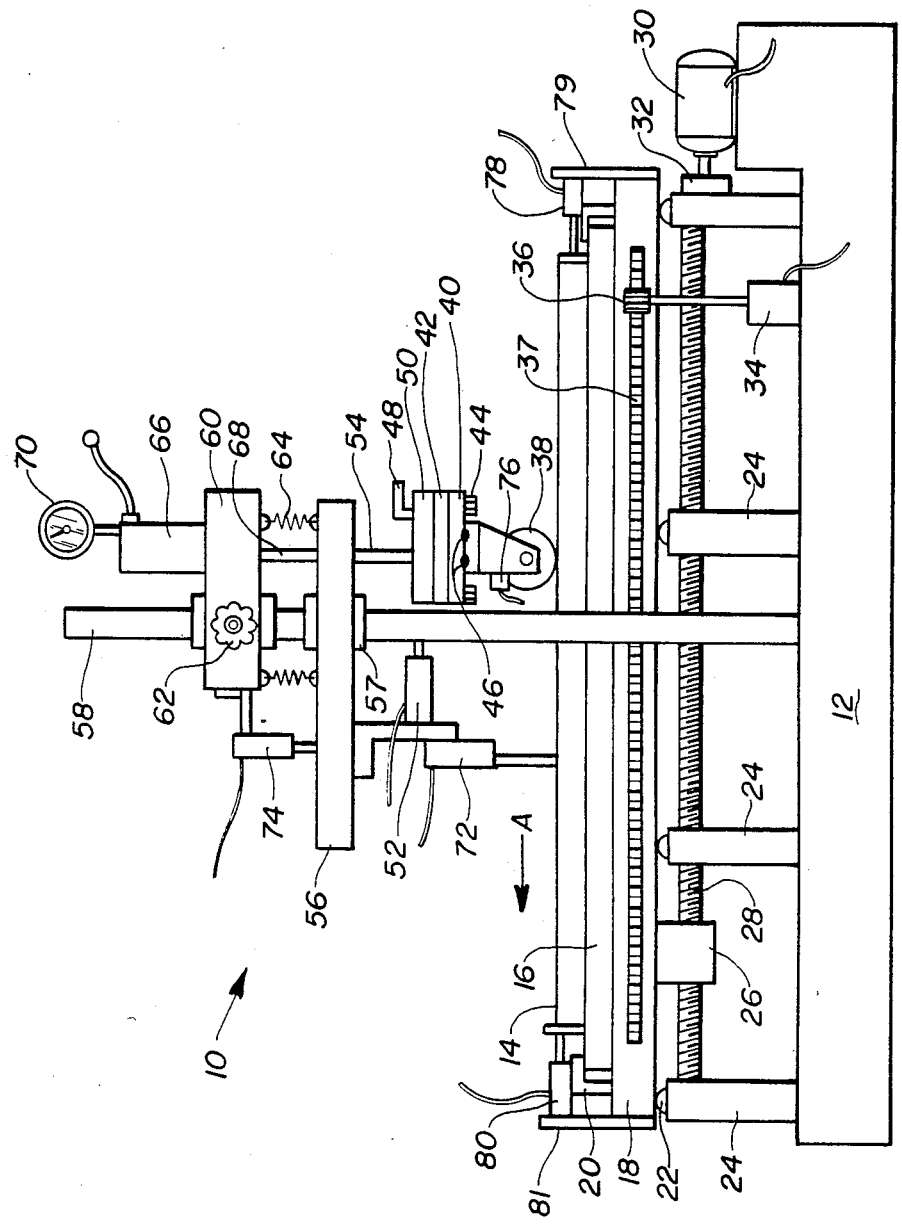

ROLLING CASTER FLOOR TESTER

This invention deals generally with testing and instrumentation and more specifically with the testing of the reaction of various floor materials to the movement of casters across them.

Casters are a common and severe problem to flooring design. Although theoretically it would seem that a rolling wheel would not scratch or damage floors, in actual practice whether or not damage occurs depends on many factors. Possibly the worst condition within common experience is that of attempting to "roll" a piece of old furniture, of an age in which wooden casters were used, on a wooden floor. In such a situation, casters are valueless, since they rarely turn. There is not enough friction between the caster and the floor surface to cause rotation.

Another more modern situation is the moving of a refrigerator over a kitchen floor. The heavy weight of the appliance is quite likely to cause the caster to sink into the floor surface slightly and leave marks where it has rolled. In fact, after a refrigerator has been sitting in one spot for several years, initial movement is quite difficult. This is usually because the long period has increased the depth to which the casters have deflected the floor material, and initially the casters must actually be rolled out of a wheel conforming depression which acts very much like a wheel chock usually used to prevent wheel movement.

To date there has been no method or device to evaluate a floor material and predict the way in which it will react to the use of casters upon it. It is this goal that the present invention addresses.

The present invention tests the reaction of floor material samples to casters under certain predetermined conditions and thereby permits the comparative evaluation of various materials as to their practical use in situations which require the use of casters.

The present invention is essentially a moving platform which passes beneath a fixture which holds a caster at a specific horizontal angle to the direction of movement and with a specific downward load force upon the caster. The test therefore measures the effects of the two major factors in the caster and floor combination, the weight factor and the angle of the caster to the direction of motion. The apparatus is also built to accommodate different diameters of casters and casters made from various materials. Although testing is usually done with a single standard width caster to eliminate another variable, the apparatus has no inherent limitations on the width of the casters tested.

Several paremeters are measured during each testing operation. Each test consists of a single pass of the sample beneath the caster, because the reaction of the sample to the test typically results in the actual deformation of the sample below the caster and therefore makes subsequent testing on the same sample of little significant value. The parameters measured are horizontal force on the caster, vertical position of the caster relative to the top surface of the floor, caster rotation, and horizontal deflection of the floor material relative to its underlying base material. Each of these parameters is measured relative to the movement of the floor material under the caster, and compilations of data and graphical presentations are produced for each test run.

The horizontal force on the caster is a basic indication of the function of the combination of the caster and floor material. This force is a reaction force to the relative movement between the caster and the floor, and while it actually represents the force necessary to push a caster load along the floor, in the test apparatus it acts in the direction of motion of the platform. In the preferred embodiment the caster is actually mounted on an elastically deflecting member and it is the measurement of the deflection which yields the actual test reading. Since the deflecting member is within its elastic limit, the reading of deflection is directly related to the force causing it.

The vertical displacement of the caster is measured directly by a measurement of the displacement of the frame to which the caster is attached. This displacement is related by the recording system to a "zero" reading which indicates the location of the top surface of the floor. The level of the top surface is a single reading made before each test run, and can be done automatically or read manually. It is used essentially to determine the initial indentation of the caster into the floor and can be measured either by the displacement with no load on the caster or by the point at which, with a given test load, the movement of the caster downward from its lifted position slows dramatically, indicating it then touched the resisting surface of the floor.

Caster rotation can be measured in several conventional ways, but one which will certainly cause no resistance of its own to the rotation is an optical encoder. The measurement of caster rotation speed, when converted to the surface speed of its circumference and then compared to the surface speed of the floor material, yields a direct indication of slippage between them.

The surface speed of the floor material is measured directly as the displacement of the moving table related to the time of the movement. A gear driven potentiometer furnishes an electrical signal which varys for each individual position of the table and thereby furnishes, not only the basis of a surface speed, but also an exact location along the test path for each observed reading.

To check on the reaction of the floor material itself to the action of the caster, readings are taken on its leading and trailing edges to measure any movement relative to the underlying base material. These readings are taken by differential transformers which sense the displacement of deflecting barriers against which the edges of the floor material rests.

In the preferred embodiment, the floor material is mounted on a moving table by its normal method. Typically, this is bonding to the underlying base material on the entire undersurface, but for some materials it means bonding only the edges. The moving table is driven by a conventional drive screw which is itself powered by an electric motor.

The test caster is mounted above the moving table on a mounting plate which permits caster replacement and this plate is attached to the deflecting member which is itself held by a loading block.

This loading block is formed as a bridge between two pillars which rise from the apparatus base and straddle the moving table. The loading block is built to move up and down freely on the pillars.

Theoretically the loading block could be simply weighted by placing individual weights upon it, but for ease of testing a pneumatic cylinder is used to produce loads which can be easily read, varied, and repeated.

The preferred embodiment also uses a computer to control the test and read and record all parameters, and thereby furnishes a completely integrated test station suitable for both design testing and sample production testing.

BRIEF DESCRIPTION OF THE DRAWING

The FIGURE is a simplified schematic diagram of one embodiment of the invention.

DETAILED DESCRIPTION OF THE INVENTION

One embodiment of the invention is depicted in the FIGURE in simplified schematic form in which test apparatus 10 is supported upon base 12. Floor material test sample 14 is bonded to base underlay 16 in the same way as floor material 14 is normally installed in use, and underlay 16 is clamped to moving table 18 by conventional clamps 20. Moving table 18 is supported above base 12 by low friction bearings 22 which are atop supports 24 mounted on base 12.

Moving table 18 is moved in direction A during the testing procedure by screw drive gear 26 attached to it and driven by drive screw 28 which is rotated by electric motor 30 through gear box 32. The position of moving table 18 is monitored by position indicator 34 which, in the preferred embodiment is a potentiometer driven by gear 36. Gear 36 is itself driven by linear gear 37 which is attached to moving table 18 and thus, in combination with position indicator 34, furnishes an electrical signal which is unique for every position of moving table 18.

Although in actual use the floor material is, of course, stationary and the caster moves, moving table 18 permits caster 38 to be fixed for ease of reading its test parameters. Top plate 40 of caster 38 is attached to test plate 42 by conventional bolts 44. It should be noted, however, that in order to achieve repeatable results, the normal free rotation of caster 38 in the horizontal plane is negated. This is typically accomplished by spot welds 46. Instead, test plate 42 is rotatable and locked by pin 48 relative to mounting plate 50. Typically, horizontal angular orientations of zero, five, ten and fifteen degrees to the direction of floor material motion are available for testing. As can readily be appreciated, the larger angles of orientation, due to the vector force of the motion transverse to the wheel circumference, cause less turning of caster 38 and more force against it.

This force against caster 38 is measured by the electrical signal produced by differential transformer 52 which actually measures the movement of mounting plate 50 against the resistance of deformable member 54. In the preferred embodiment deformable member 54 is a metal bar with some depth transverse to direction of motion A so that it will prevent angular deflection of caster 38 and will merely move slightly in the same vertical plane as caster 38. Actually the deflection of member 54 is so slight that no perceptable visible movement occurs but what does occur is sufficient to produce a valid measure of the force causing it.

In order to simulate a caster with a weighted load, deflecting member 54 is itself attached to loading plate 56 which rides freely on bearing 57 up and down pillar 58, which is itself anchored to base 12. Pillar 58 has a matching counterpart (not seen) on the other side of base 12, and loading plate 56 and header 60, in fact, form a bridge-like structure across moving table 18 with caster 38 located between the pillars. Header 60 is fixed in placed on pillar 58 by locking bolt 62, which permits a height adjustment for varying caster diameters. Loading plate 56 is optionally attached to header 60 by counter-balancing connectors, such as springs 64. Springs 64 are actually adjusted to a known tension which is used to aid in determining the loading weight for the test. For instance, if header 60 is lowered so that, with stretched springs 64, caster 38 just touches the top surface of floor material 14, any weight then placed on loading plate 56 is the actual load weight on caster 38.

In actual practice, however, the load weight is best accomplished by using pneumatic cylinder 66 acting through piston 68 to furnish the loading force against loading plate 56 and which is readable on gauge 70. The parameters of each test run are therefore set by the air pressure applied to pneumatic cylinder 66, the horizontal angular orientation of test plate 42, and the diameter and material of caster 38. While the speed of motor 30 could also be variable it appears to be most advantageous to use a single speed, which simulates a typical field use, for all testing and therefore further standardize material testing.

All the readings taken by test apparatus 10 are dynamic reading taken while table 18 is moving, except for one. It is particularly advantageous for visualizing the graphical results of vertical movement of caster 38 to know the location of the unloaded top surface of floor material 14, because most floor materials compress at least some amount when loaded. To provide this top surface location, differential transformer 72 is used to measure the position of the top surface of floor 14 when unloaded so that it can be compared to the location of the bottom of caster 38 after loading and compressing floor material 14.

During the test, as moving table 18 moves in direction A, caster 38 is subjected to a force in the same direction which is measured, as described above, by differential transformer 52. However, caster 38 is also quite likely to move vertically, and this motion, which lifts loading plate 56, is measured by differential transformer 74. The rotation of caster 38 is at the same time monitored by encoder 76. A recording instrument (not shown) is attached to each of these devices to record the electrical signals generated and compare them to the electrical signal produced by position indicator 34. Interpretation of this data yields detailed information on the reaction of a particular sample in terms of friction acting upon a particular caster and damage from it. In the preferred embodiment the recording instrument used is a computer which can both tabulate and graph the results, and the reading from differential transformer 72 permits a zero reference on the graph which simulates a profile of the material top surface under the loading weight of the caster.

One of the more dramatic results of the use of test apparatus 10 is the recognition that, for some floor samples which are unbonded to base underlay 16, a bubble of floor material can form on the leading edge of caster 38 and randomly catch underneath caster 38 causing a lifting of the caster and a resulting foldover on the floor material. Differential transformers 78 and 80, which monitor the movement of barrier edges 79 and 81 respectively, aid in the recognition of such phenomena and others such as linear stretching or compressing of floor material 14. These dimensional changes are transmitted to barrier edges 79 and 81, measured by differential transformers 78 and 80, and recorded along with the other data.

Test apparatus 10 therefore is able not only to simulate caster movement across the sample under prescribed conditions, but also to measure both the frictional reaction between the caster and the floor material and also the effects of the caster on the floor material. Moreover, the measurement of the floor material distortion includes not only compression through the thickness of the material and distortions in that dimension, but also linear stretching or compression.

It is to be understood that the form of this invention as shown in the FIGURE is merely a preferred embodiment. Various changes may be made in the function and arrangement of parts; equivalent means may be substituted for those illustrated and described; and certain features may be used independently from others without departing from the spirit and scope of the invention as defined in the following claims.

For example, displacement measuring means other than differential transformers could be used. Alternatively, one differential transformer or other displacement measuring means may be adapted to process the data that, in the preferred embodiment, is processed by two such displacement measuring means. Moreover, other means to measure the location of the top surface of the floor material could also be substituted. In addition, the moving table could be supported above the base by split bearings which are mounted on rods running parallel to the drive screw and which are attached to the base.

What is claimed is:

1. A testing apparatus to test the effects of casters upon floor material comprising:
   base means;
   first support means attached to the base means;
   moving table means supported by the first support means and freely moveable in a linear direction;
   table drive means attached to the moving table means and capable of driving the moving table means in a linear direction;
   sample retaining means attached to the moving table means and capable of holding a floor material sample upon the moving table means;
   second support means attached to the base means;
   loading plate means moveably connected to the second support means so as to permit movement of the loading plate means in a vertical direction;
   caster test plate means attached to the loading plate means to which a caster may be attached;
   caster means attached to the caster test plate means and capable of resting upon the top surface of a floor material sample upon the moving table means;
   horizontal force measurement means, upon which the caster means acts, measuring horizontal forces acting upon the caster means;
   variable weight loading means acting on the loading plate means and capable of varying the downward force upon the caster means; and
   horizontal angle determining means attached to the caster means and providing at least one angle relative to the motion of the moving table means other than zero at which the caster means may be oriented.

2. The testing apparatus of claim 1 further including vertical deflection measuring means capable of measuring the vertical displacement of the caster means relative to the moving table means.

3. The testing apparatus of claim 1 further including sample surface measuring means capable of measuring the vertical displacement relative to the caster means of the top surface of a floor material sample upon the moving table means.

4. The testing apparatus of claim 1 further including linear position indictor means capable of generating an electrical signal which is unique for every linear position of the moving table means.

5. The testing apparatus of claim 1 further including angle varying means attached to the caster means and providing at least two horizontal angles relative to the motion of the moving table means at which the caster means may be oriented.

6. The testing apparatus of claim 1 further including sample distortion measurement means for measuring the direction of a floor material sample in the direction of motion of the moving table means.

7. The testing apparatus of claim 1 wherein the variable weight loading means is a pneumatic cylinder attached to the second support means and operating a piston against the loading plate means.

8. The testing apparatus of claim 1 wherein the table drive means is a drive screw driven by an electric motor and a screw drive gear attached to the moving table means.

9. The testing apparatus of claim 1 further including caster rotation measuring means upon which the caster acts and which provides an electrical signal related to the rotation of the caster.

* * * * *